US00PP20552P3

(12) United States Plant Patent
Shaw et al.

(10) Patent No.: US PP20,552 P3
(45) Date of Patent: Dec. 15, 2009

(54) STRAWBERRY PLANT NAMED 'PORTOLA'

(50) Latin Name: *Fragaria×ananassa*
Varietal Denomination: Portola

(75) Inventors: Douglas V. Shaw, Davis, CA (US); Kirk D. Larson, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 134 days.

(21) Appl. No.: 11/983,159

(22) Filed: Nov. 6, 2007

(65) Prior Publication Data

US 2009/0144866 P1 Jun. 4, 2009

(51) Int. Cl.
*A01H 5/00* (2006.01)

(52) U.S. Cl. ..... Plt./209

(58) Field of Classification Search ..... Plt./209, Plt./208

See application file for complete search history.

*Primary Examiner*—Susan B McCormick Ewoldt
(74) *Attorney, Agent, or Firm*—Townsend and Townsend and Crew LLP

(57) ABSTRACT

This invention relates to a new and distinctive day-neutral type strawberry designated as 'Portola'.'Portola' is a day-neutral (everbearing) cultivar similar to 'Diamante' (U.S. Plant Pat. No. 13,079) but with higher yield and better quality fruit, better disease resistance and better flavor; it is similar to 'Albion' (U.S. Plant Pat. No. 16,228) for fruit quality but with higher yield, and larger and lighter colored fruit.

3 Drawing Sheets

Genus and species: The strawberry cultivar of this invention is botanically identified as *Fragaria×ananassa* Duch.

Variety denomination: The variety denomination is 'Portola'.

BACKGROUND OF THE INVENTION

This invention relates to a new and distinctive day-neutral type cultivar designated as 'Portola', which resulted from a cross performed in 2001 between advance selections Cal 97.93-7 and Cal 97.209-1. 'Portola' was first fruited near Winters, Calif. in 2002, where it was selected, originally designated Cal 1.206-5, and propagated asexually by runners. Following selection and during testing the plant of this selection was designated 'CN224' and, later for introduction into commerce, 'Portola'. Asexual propagules from this original source have been tested at a Watsonville strawberry research facility, an Irvine, Calif. research station, and to a limited extent in grower fields starting in 2005.

BRIEF SUMMARY OF THE INVENTION

'Portola' is a day-neutral (everbearing) cultivar similar to 'Diamante' (U.S. Plant. Pat. No. 10,435) but with higher yield and better quality fruit, better disease resistance and better flavor; it is similar to 'Albion' (U.S. Plant Pat. No. 16,228) for fruit quality but with higher yield, and larger and lighter colored fruit.

BRIEF DESCRIPTION OF THE DRAWINGS

The figures depict various characteristics of the 'Portola' cultivar.

DETAILED DESCRIPTION OF THE INVENTION

Figure 1:
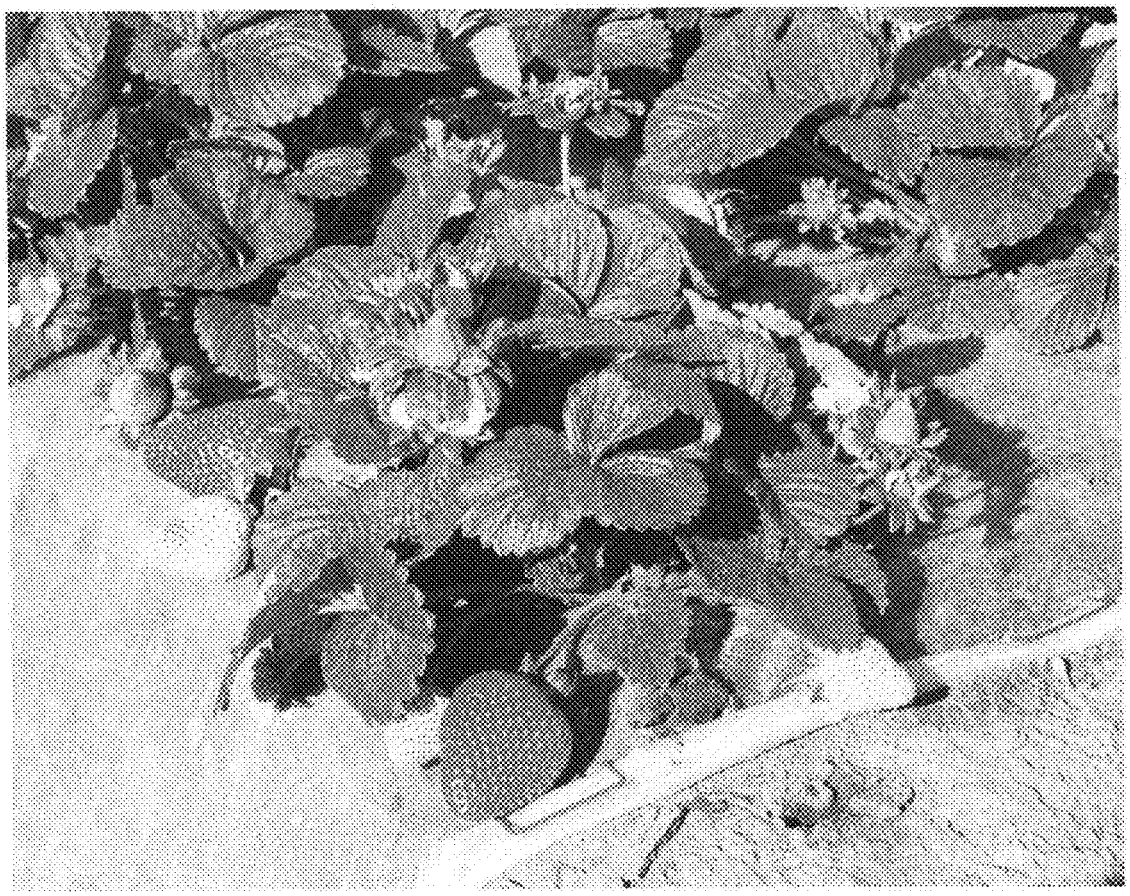
FIG. 1 shows the general flowering and fruiting characteristics of the plant in a field planting.
Figure 2:
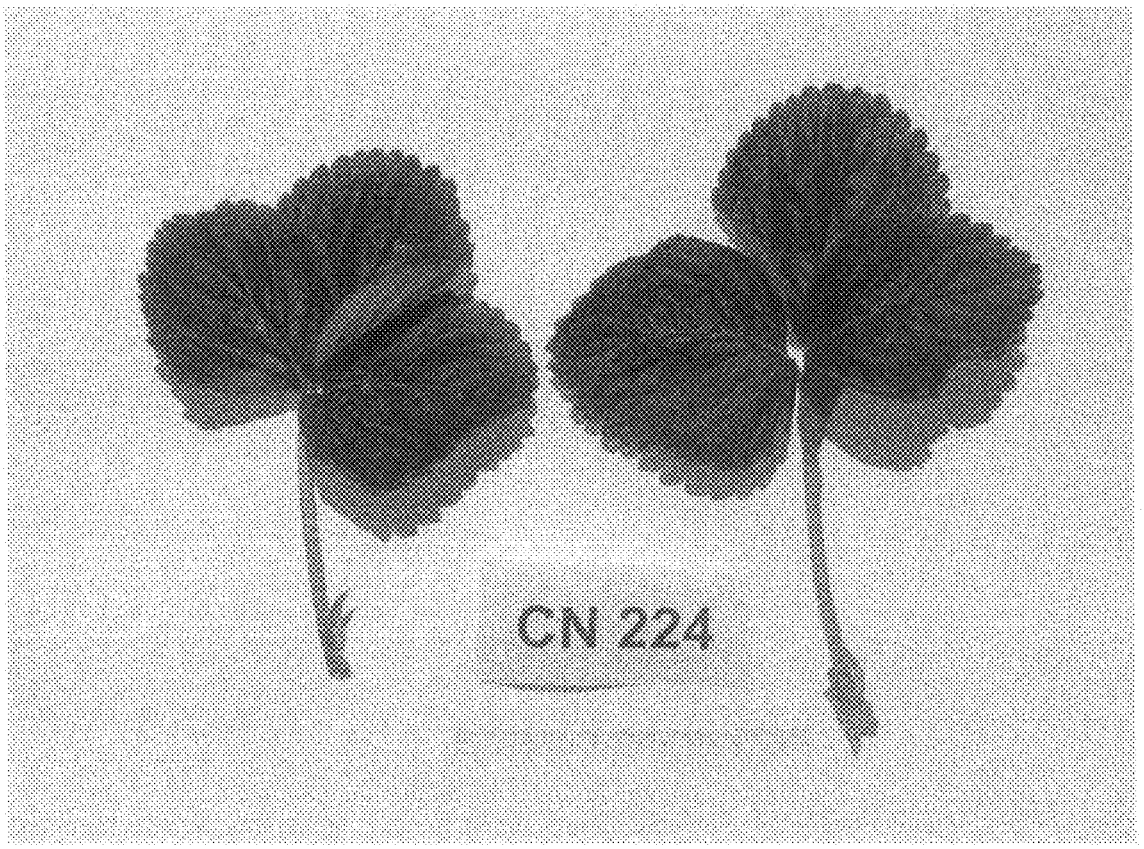
FIG. 2 shows a typical leaf at mid-season.
Figure 3:
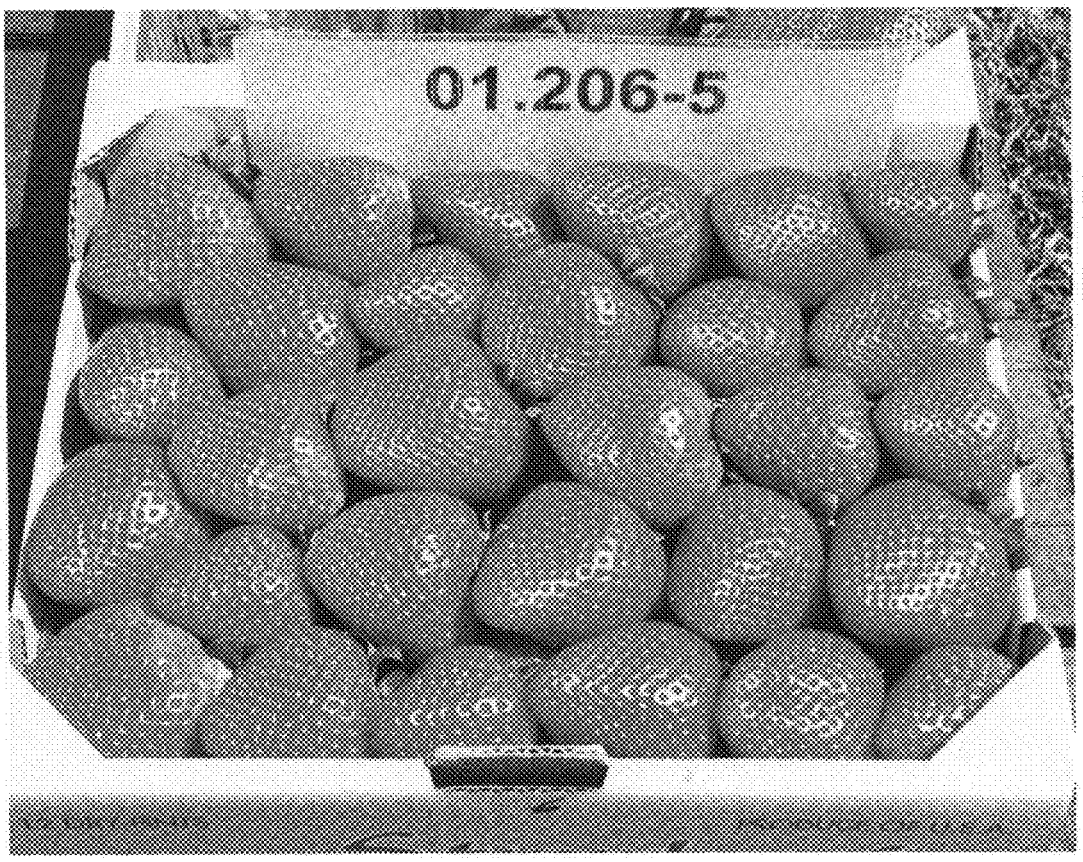
FIG. 3 shows a representative mid-season fruit.

'Portola' is typical of day-neutral strawberry cultivars and produces fruit regardless of day length when treated appropriately in arid, subtropical climates. 'Portola' is moderate to strong in expressing the day-neutral character, being stronger in flowering response to 'Diamante' (U.S. Plant Pat. No. 10,435) and Albion (U.S. Plant Pat. No. 16,228), and more similar in flowering to 'Fern' (U.S. Plant Pat. No. 5,267) or 'Irvine' (U.S. Plant Pat. No. 7,172). The production pattern for 'Portola' is similar to that for 'Albion', although it is earlier to initiate production. 'Portola' fruit is of more uniform size than parent Cal 97.209.1. 'Portola' has firmer fruit and more evenly shaped fruit compared to Cal 97.93-7. 'Portola' will be of special interest for winter plantings and in summer plantings where 'Diamante' and 'Albion' have been successful. It is expected to perform especially well in spring and summer planting systems aimed at fall fruit production.

Plants and foliage: Fruiting plants of 'Portola' are similar in morphology to 'Diamante' and 'Albion' although somewhat larger throughout the season; 'Portola' plants are similar in size to plants of 'Aromas' but more dense. Comparative statistics for foliar characters near mid-season are given for 'Portola' and the three comparison cultivars in Table 1. Individual leaflets for 'Portola' are similar in shape and size to the comparison cultivars. Leaves (including petioles) for 'Portola' are longer than those for 'Diamante' and 'Albion', mostly due to greater petiole length. Petioles are generally thinner than those of the comparison cultivars and tend to have heavy pubescence. The adaxial (upper) and abaxial (lower) surfaces of leaves for 'Portola' are similar in color to the comparison cultivars at mid season, but slightly lighter early in the season. Leaves of 'Portola' have similar concavity to 'Aromas', 'Diamante', and 'Albion'.

Disease and pest reaction: 'Portola' is moderately resistant to powdery mildew (*Sphaerotheca macularis*), Anthracnose crown rot (*Colletotrichum acutatum*), and *Verticillium* wilt (*Verticillium dahliae*); it is very resistant to *Phytophthora* crown rot (*Phytophthora cactorum*) and common leaf spot (*Ramularia tulasnei*) (Table 3). When treated properly, it has tolerance to two-spotted spider mites (*Tetranychus urticae*) equal to that for the comparison cultivars. 'Portola' is tolerant to strawberry viruses encountered in California.

TABLE 1

Foliar and plant characteristics for 'Portola', 'Aromas', 'Diamante', and 'Albion'.

| | Cultivar | | | |
|---|---|---|---|---|
| Foliar Character | 'Aromas' | 'Diamante' | 'Albion' | 'Portola' |
| Plant height (mm) | | | | |
| mean | 272 | 220 | 223 | 267 |
| range | 240-300 | 190-240 | 170-290 | 240-300 |
| Plant spread (mm) | | | | |
| mean | 323 | 316 | 295 | 313 |
| range | 300-360 | 265-385 | 270-315 | 295-335 |
| Midtier leaflet Length (mm) | | | | |
| mean | 79 | 78 | 70 | 71 |
| range | 70-90 | 60-90 | 60-80 | 65-80 |
| Width (mm) | | | | |
| mean | 74 | 77 | 68 | 69 |
| range | 70-80 | 55-90 | 60-80 | 60-90 |
| Midtier leaf Length (mm) | | | | |
| mean | 113 | 99 | 99 | 107 |
| range | 100-120 | 80-120 | 90-110 | 100-120 |
| Width (mm) | | | | |
| mean | 135 | 134 | 122 | 136 |
| range | 120-150 | 90-150 | 105-135 | 120-150 |
| Leaf components Petiole length (mm) | | | | |
| mean | 174 | 114 | 122 | 159 |
| range | 140-210 | 100-130 | 95-180 | 110-215 |
| Petiole diameter (mm) | | | | |
| mean | 4.5 | 5.2 | 4.9 | 3.9 |
| range | 4-6 | 4-7 | 4-6 | 3-5 |
| Petiolule length (mm) | | | | |
| mean | 6.6 | 5.2 | 6.7 | 7.0 |
| range | 4.3-7.5 | 4.0-7.6 | 5.0-8.0 | 5-8 |
| # leaflets/leaf | 3 | 3 | 3 | 3 |
| Leaf convexity | some flat, most slight concave | some flat, most slight concave | some flat, most slight concave | some flat, most slight concave |
| Serrations | | | | |
| number/leaf | 19.9 | 20.2 | 23.3 | 24.4 |
| range | 16-24 | 16-24 | 21-27 | 21-28 |
| shape | rounded to semi-pointed | rounded to semi-pointed | semi-pointed | most rounded, some semi-pointed |

TABLE 1-continued

Foliar and plant characteristics for 'Portola', 'Aromas', 'Diamante', and 'Albion'.

| | Cultivar | | | |
|---|---|---|---|---|
| Foliar Character | 'Aromas' | 'Diamante' | 'Albion' | 'Portola' |
| Leaf pubescence | moderate | moderate-heavy | moderate | heavy |
| Petiole pubescence density | Moderate-heavy | heavy | heavy | heavy |
| direction | per-pendicular | per-pendicular | per-pendicular | per-pendicular |
| Petiole color (Munsell) | 5 GY 8/8 | 7.5 GY 9/4 | 5 GY 8/8 | 5 GY 8/8 |
| Stipule length (mm) | | | | |
| mean | 34.2 | 31.6 | 32.5 | 33.4 |
| range | 30-39 | 22-36 | 24-37 | 29-40 |
| Stipule color | | | | |
| core | 7.5 GY 8/7 | 7.5 GY 8/7 | 5 GY 8/7 | 2.5 GY 8/9 |
| margins | 2.5 GY 9/3 | 5 GY 6/8 | 5 GY 6/8 | 5 GY 7/10 |
| Stolon base diameter (mm) | 3.0 | 3.2 | 3.0 | 3.2 |
| Stolons per nursery mother plant | 33.0 | 29.0 | 26.9 | 32.0 |
| Venation | | | | |
| pattern | pinnate | pinnate | pinnate | pinnate |
| color | 2.5 GY 5/5 | 10 GY 5/5 | 2.5 GY 6/8 | 10 Y 6/7 |

Flowering, fruiting, fruit, and production characteristics: 'Portola' is similar to other California day-neutral cultivars (e.g., 'Diamante' and 'Albion') in that it will flower independently of day length, given appropriate temperature and horticultural conditions. Comparative statistics for flower and fruit characters near mid-season are given for 'Portola' and three other cultivars in Table 4. The primary flowers for 'Portola' are slightly larger than those of the 'Aromas' and 'Diamante' but smaller than those of 'Albion'. The calyx for 'Portola' is distinctly larger than the corolla on primary fruit; the sepals are similar in length and shape to those of the comparison cultivars. The calyx for 'Portola' varies in position but is usually less reflexed than for 'Aromas' or 'Diamante', much less than that of 'Albion'. The fruit shape for 'Portola' can vary but is typically a medium to short and highly symmetrical conic. It is easily distinguished by fruit shape from 'Aromas' (shortened and rounded conic), 'Diamante' (usually a flat conic) or 'Albion' (long conic); 'Portola' usually has a greater proportion of symmetrical fruit than the comparison cultivars, especially early in the fruiting season. External fruit color for 'Portola' is slightly lighter than 'Aromas' or 'Albion', distinctly darker than for 'Diamante'; internal color is somewhat darker with greater red pigment than for the comparison cultivars (Table 2). Achenes vary from yellow to dark red, but are usually red, and range from even with the fruit surface to slightly indented.

'Portola' has been tested under a variety of cultural regimes, and optimal performance is obtained when nursery treatments and nutritional programs similar to those for 'Albion', 'Diamante', and 'Aromas' are used. In general, 'Portola' is more vigorous than the comparison cultivars and is less sensitive to low chilling. 'Portola' is distinctly stronger in day-neutrality than the comparison cultivars and produces greater quantities of fruit when established with spring or summer plantings of long-term cold stored plant material. 'Portola' retains excellent fruit quality in summer planting systems.

When treated with appropriate planting regimes, 'Portola' has larger fruit and produces greater individual-plant yield than any of the comparison cultivars (Table 5). 'Portola' has a similar production pattern to 'Albion' with most cultural treatments, although it is substantially more adapted to early-season winter planting. Commercial appearance ratings have been similar to or higher than those for all of the comparison cultivars, especially 'Aromas'; these superior appearance scores translate directly into a larger fraction of marketable fruit than is produced by the comparison cultivars. Fruit for 'Portola' is substantially firmer than fruit from 'Aromas', similar in firmness to the other comparison cultivars. Subjectively, 'Portola' has outstanding flavor. The fruit will be exceptional for both fresh market and processing, and will be useful for home garden purposes.

TABLE 2

Foliar and fruit color characteristics for 'Portola' and three comparison cultivars.

| Color Character | Cultivar 'Aromas' | 'Diamante' | 'Albion' | 'Portola' |
|---|---|---|---|---|
| Leaf color (CIELAB) Adaxial | | | | |
| L* | | | | |
| mean | 35.1 | 34.8 | 34.7 | 34.3 |
| range | 32.7-37.7 | 32.6-36.8 | 32.8-36.7 | 31.6-35.5 |
| a* | | | | |
| mean | −10.6 | −10.4 | −9.8 | −9.8 |
| range | −8.2--14.0 | −8.7--11.9 | −9.4--11.3 | −8.0--11.5 |
| b* | | | | |
| mean | 13.8 | 13.8 | 12.8 | 13.1 |
| range | 11.2-18.1 | 12.2-16.6 | 10.7-15.6 | 11.0-15.7 |
| Munsell | 7.5 GY 4/4 | 5 GY 4/3 | 5 GY 4/3 | 5 GY 4/3 |
| Abaxial | | | | |
| L* | | | | |
| mean | 52.4 | 51.1 | 50.6 | 52.4 |
| range | 50.6-54.1 | 49.7-52.2 | 43.7-53.1 | 51.5-54.1 |
| a* | | | | |
| mean | −11.6 | −12.8 | −12.4 | −11.6 |
| range | −10.7--13.6 | −11.6--14.9 | −8.6--11.4 | −10.3--13.6 |
| b* | | | | |
| mean | 17.3 | 19.5 | 17.2 | 17.3 |
| range | 14.3-23.2 | 15.3-23.5 | 14.5-19.6 | 15.9-23.2 |
| Munsell | 10 GY 7/8 | 7.5 GY 6/8 | 7.5 GY 8/7 | 10 GY 7/8 |
| Fruit color (CIELAB) External | | | | |
| L* | | | | |
| mean | 34.2 | 40.8 | 36.5 | 34.3 |
| range | 31.2-38.3 | 35.5-45.4 | 32.8-40.1 | 31.4-37.2 |
| a* | | | | |
| mean | 33.9 | 36.7 | 33.3 | 35.7 |
| range | 31.5-38.6 | 35.6-40.2 | 28.3-36.2 | 31.0-39.9 |
| b* | | | | |
| mean | 14.1 | 21.2 | 17.6 | 15.9 |
| range | 9.1-16.5 | 18.8-25.7 | 12.2-24.9 | 13.4-20.6 |

TABLE 2-continued

Foliar and fruit color characteristics for 'Portola' and three comparison cultivars.

| Color Character | Cultivar 'Aromas' | 'Diamante' | 'Albion' | 'Portola' |
|---|---|---|---|---|
| Munsell | 2.5 R 4/10 | 5 R 5/13 | 5 R 3/7 | 5 R 4/12 |
| Internal | | | | |
| L* | | | | |
| mean | 61.6 | 65.6 | 57.9 | 50.9 |
| range | 59.5-67.7 | 58.8-67.2 | 43.3-62.9 | 45.2-56.7 |
| a* | | | | |
| mean | 14.7 | 5.6 | 19.0 | 30.4 |
| range | 7.6-19.2 | 3.0-9.5 | 7.9-27.7 | 24.2-36.6 |
| b* | | | | |
| mean | 20.2 | 15.8 | 21.0 | 28.0 |
| range | 16.1-22.5 | 14.5-18.2 | 13.2-27.2 | 23.7-31.4 |
| Munsell | 5 R 6/11 | 10 R 7/9 | 7.5 R 4/11 | 7.5 R 5/13 |
| Achene color Munsell | 7.5 R 4/11 | 7.5 R 4/11 | 10 R 5/6 | 10 R 4/9 |

*CIELAB is the abbreviation of the international color system known as "Commission Internationale De L'Eclairage" 1978. For recommendations concerning uniform color spaces, color difference equations, and psychometric color terms see Supplement No. 2 of CIE Publication No. 15, Paris.

TABLE 3

Disease resistance scores for 'Portola' and three comparison cultivars; *Phytophthora* and *Verticillium* scores were obtained in evaluations conducted in 2004-2006, *Colletotrichum* was evaluated in 2005-2006.

| Genotype | *Phytophthora* Resistance Score (5 = best) | *Verticillium* Resistance Score (5 = best) | *Colletotrichum* Resistance Score (5 = best) |
|---|---|---|---|
| 'Aromas' | 4.0 | 4.5 | 2.4 |
| 'Diamante' | 2.0 | 2.8 | 2.6 |
| 'Albion' | 4.3 | 3.8 | 3.1 |
| 'Portola' | 4.4 | 3.3 | 2.6 |

TABLE 4

Flower and fruit characters for 'Portola' and three comparison cultivars.

| Character | Cultivar 'Aromas' | 'Diamante' | 'Albion' | 'Portola' |
|---|---|---|---|---|
| Petal number | | | | |
| mean | 5.5 | 5.4 | 5.6 | 6.8 |
| range | 5-7 | 5-6 | 5-7 | 5-8 |
| Petal shape | | | | |
| apex | truncate to slightly obtuse | truncate to slightly obtuse | truncate to slightly obtuse | truncate to slightly obtuse |
| base | attenuate | attenuate | attenuate | attenuate |
| margin | entire | entire | entire | entire |
| Petal length (mm) | | | | |
| mean | 10.1 | 9.2 | 9.6 | 11.1 |
| range | 8-11 | 7-13 | 8-11 | 8-13 |
| Petal width (mm) | | | | |
| mean | 11.8 | 10.6 | 9.0 | 12.4 |
| range | 10-13 | 10-13 | 7-10 | 9-14 |

TABLE 4-continued

Flower and fruit characters for 'Portola' and three comparison cultivars.

| Character | Cultivar 'Aromas' | 'Diamante' | 'Albion' | 'Portola' |
|---|---|---|---|---|
| Flower position (relative to foliage) | most even some exposed | most even some internal and exposed | most exposed, some even | most exposed, some even |
| Calyx diam. (mm) | | | | |
| mean | 31.3 | 32.0 | 37.5 | 36.0 |
| range | 28-33 | 25-41 | 31-48 | 31-42 |
| Corolla diam. (mm) | | | | |
| mean | 31.2 | 23.9 | 27.8 | 32.2 |
| range | 26-35 | 18-31 | 23-33 | 24-39 |
| Sepal length (mm) | | | | |
| mean | 12.3 | 12.1 | 14.1 | 12.5 |
| range | 8-15 | 10-15 | 11-18 | 9-15 |
| Sepal width (mm) | | | | |
| mean | 6.4 | 6.7 | 6.6 | 7.3 |
| range | 3-9 | 5-9 | 4-10 | 5-9 |
| Sepal color (Munsell) | 7.5 GY 6/8 | 5 GY 5/6 | 2.5 GY 6/8 | 5 GY 5/6 |
| Pedicel length (mm) | | | | |
| mean | 172 | 140 | 218 | 225 |
| range | 112-230 | 110-165 | 180-270 | 200-240 |
| Pedicel diameter (mm) | | | | |
| mean | 4.4 | 5.3 | 3.1 | 4.3 |
| range | 4-6 | 4-6 | 2-4 | 3-6 |
| Pedicel color | 5 GY 6/8 | 5 GY 7/10 | 5 GY 6/8 | 5 GY 6/8 |
| Fruit shape | | | | |
| Fruit length (mm) | | | | |
| mean | 46.6 | 46.4 | 61.7 | 50.4 |
| range | 42-52 | 39-50 | 50-76 | 43-57 |
| Fruit width (mm) | | | | |
| mean | 39.4 | 40.7 | 46.6 | 47.7 |
| range | 37-43 | 38-46 | 37-52 | 43-54 |
| Length/width | | | | |
| ratio | 1.2 | 1.1 | 1.3 | 1.1 |
| range | 1.0-1.4 | 1.0-1.2 | 1.2-1.5 | 1.0-1.2 |
| subjective | mostly medium to short flat conic | rounded to flat conic | most long sym-metrical conic | Medium-short sym-metrical conic |

TABLE 4-continued

Flower and fruit characters for 'Portola' and three comparison cultivars.

| Character | Cultivar 'Aromas' | 'Diamante' | 'Albion' | 'Portola' |
|---|---|---|---|---|
| Primary/secondary fruit comparison | | | | |
| size (subjective) | 60-80% | 60-80% | 60-70% | 75-85% |
| shape | similar shape | similar shape | similar shape | similar shape |
| Extent/size of hollow core | small-absent | small-absent | small-medium | small-medium |
| Calyx | | | | |
| position | indented-even with neck | even-indented | even-reflexed | even-indented |
| size relative to fruit | equal or greater than fruit diameter | equal or greater than fruit diameter | equal or greater than fruit diameter | equal or greater than fruit diameter |
| Seed position | indented-extruded | indented-even | indented-extruded | indented-even |
| Adherence of Calyx to Fruit | inter-mediate | inter-mediate | inter-mediate | inter-mediate |

Flower measurements and fruit measurements obtained May 9–Jun. 6, 2006, subjective observations obtained Jul. 31, 2006.

TABLE 5

Performance 'Portola' and three comparison cultivars evaluated at the Watsonville Research Facility in 2005-7. All plants for these trials were harvested from a commercial nursery near Macdoel, CA on October 15-16, and transplanted after 18-21 days supplemental storage. Fruit harvest was initiated in early April and continued through the first week of October. (52" 2-row beds, 17,300 plants/acre).

| Item | Yield (g/plant) | Appearance Score (5 = best) | Fruit Size (g/fruit) | Firmness |
|---|---|---|---|---|
| 'Aromas' | 3,108 | 3.1 | 27.0 | 9.6 |
| 'Diamante' | 2,653 | 3.5 | 31.2 | 11.0 |
| 'Albion' | 2,461 | 3.9 | 30.5 | 11.1 |
| 'Portola' | 3,336 | 3.6 | 32.0 | 10.2 |

What is claimed is:

1. A new and distinct cultivar of strawberry plant having the characteristics substantially as described and illustrated herein.

* * * * *